(12) United States Patent
Shau et al.

(10) Patent No.: US 7,179,874 B2
(45) Date of Patent: Feb. 20, 2007

(54) BIODEGRADABLE CATIONIC POLYMER

(75) Inventors: Min-Da Shau, Kaohsiung (TW);
Jong-Yuh Cherng, Tainan (TW);
Tsung-Fu Yang, Changhua (TW);
Wei-Kuo Chin, Taipei (TW)

(73) Assignee: Chia Nan University of Pharmacy and Science (TW)

( * ) Notice: Subject to any disclaimer, the term of this patent is extended or adjusted under 35 U.S.C. 154(b) by 318 days.

(21) Appl. No.: 10/717,713

(22) Filed: Nov. 21, 2003

(65) Prior Publication Data

US 2005/0112203 A1    May 26, 2005

(51) Int. Cl.
*C08F 20/54* (2006.01)
(52) U.S. Cl. .............................. 526/303.1; 526/307.2
(58) Field of Classification Search ............. 526/303.1, 526/307.2
See application file for complete search history.

Primary Examiner—Robert D. Harlan

(57) ABSTRACT

A biodegradable cationic polymer is disclosed. The biodegradable cationic polymer of the invention has amino groups in the backbone and side chains, self-assembles cationic complexes with nucleic acids, and delivers nucleic acids into a cell by endocytosis. The biodegradable cationic polymer of the invention also has very low cytotoxicity. Methods of making and using the biodegradable cationic polymer are further disclosed.

9 Claims, 7 Drawing Sheets

BIODEGRADABLE CATIONIC POLYMER

FIELD OF INVENTION

The present invention relates to a biodegradable cationic polymer. More particularly, the present invention relates to the biodegradable cationic polymer for delivering nucleic acids into a cell, and methods of making and using the biodegradable cationic polymer.

BACKGROUND OF THE INVENTION

"The Achilles heel of gene therapy is gene delivery", said by Inder M. Verma, the famous biologist of the Salk institute in San Diego, Calif., USA. While delivering an exogeneous gene into a cell, scientists must compress the corresponding deoxyribonucleic acid (DNA) into a small package absorbed by the cell. But that is not enough. The gene must be protected from cellular enzyme digestion. While the gene arrived into the nucleus, the gene must remain in an active form. For the reasons that the DNA carrying negative charges, the size of itself, and nucleases in the blood, if the naked DNA is directly administrated, the naked DNA may suffer nucleolytic degradation prior to its delivery to the target, resulting in the insufficient therapy. However, this problem can be overcome by utilizing a suitable carrier to enhance DNA into the nucleus.

Common carriers for gene therapy include viral and non-viral vectors. Common viral vectors include retroviral and adenoviral vectors. Ribonucleic acid (RNA) viruses with envelope are the most popular in retroviral vectors. The RNA viruses generate double-stranded (ds) DNA by reverse transcriptase action, and then integrate into the host chromosomes, to achieve characteristics of gene therapy and stable expression.

Viral carriers have better delivery efficiency and expression in vivo as their advantages, but there are some drawbacks existed in their potential risks. For example, it must be considered that random insertion may induce undesirably insertional mutagenesis in using viruses. There are replication competent viruses (RCV) may be generated due to gene recombination happened in packaging the viral particles, or immune responses may be induced by pathogenic viruses which are recombined by viral vectors and latent viruses. Furthermore, it is difficult to produce viral vectors by cell culturing, so it is not easy to produce viral vectors in scale.

The approaches by non-viral vectors, such as liposomes or directly injecting DNA into a cell by microinjection or a gene gun, can avoid possible risks and side effects caused by viral vectors. "Lipofection" uses some liposomes made of nucleic acids and phospholipids with no charge or polarity in various ratios to pack DNA therein, which would pass through the cell membrane and introduce DNA into a cell or tissue by endocytosis. A type of liposome, for examples, linked with a specific antibody, or a ligand of a receptor chemically linked with poly-lysine as a DNA binding domain, can improve to facilitate specificity of DNA delivered to the specific cell. However, the transfection efficiency of DNA delivered by liposomes is not efficient, and most DNA is degraded inside endosomes, so the actual DNA expression in the nucleus is limited.

On one hand, investigators try to understand and reduce the risk of viral vectors used in the gene therapy, and on the other hand, they designate alternative approaches by utilizing polymers where plasmid DNA is embedded in. Mark E. Davis of the professor and Sue J. Huang, in California Institute of Technology, USA, disclose a cationic polymer derived from β-Cyclodextrin (CD). See, Bioconjugate Chemistry (2002) 13, page 630. This kind of material, which is non-toxic, non-immunogenic, dissolved in water, and can be modified on the surface of CD particle by linking with polyethylene glycol (PEG) having adamantine, for CD/DNA nanoparticles with uniform size, and may not form aggregate with proteins in the plasma to lose its biological potential. The PEG modifies the surface of CD particles, and provides "chemical hook" to bind to other substance that can lead CD particles or delivery gene to a specific cell.

Methods of making and using poly[α-(4-aminobutyl)-L-glycolic acid] (PAGA), which is an analogue of poly-L-lysine, for delivering a gene into a cell are disclosed in U.S. Pat. No. 6,217,912. PAGA is grafted with PEG, to form block copolyines with other polymers, such as poly-L-lysine, polyarginine, polyorthithine, histidine, avidin, protamines, polylactides, or polylactic/glycolic acid, and provided complexes with nucleic acids for delivering a gene into a cell.

U.S. Pat. No. 6,083,741 and PCT Pub. No. WO96/15811 disclose a conjugate which is formed with a polylysine coupling to a integrin receptor binding moiety comprising a peptide of the sequence arginine-glycine-asparagine (RGD). The sequence RGD binds specifically integrin receptors on the tissue, and leads DNA/Polylysine complexes into cells in the target tissue.

U.S. Pat. No. 5,965,404 and T.W. Pat. No. 496,898 disclose a process of introducing nucleic acid into mammalian cells, in which combines DNA with a partial amount of polylysine of various lengths, and subsequently the rest of polylysine, in majority portion, is added into complexes, and optionally add chloroquine in the presence of ethylene glycol and/or glycerol, for introducing nucleic acids into primary cells to obtain stably transformed cells. Thereby, polycations, such as polylysine, can form complexes with DNA, or conjugates of polycations and transferrin may complexate with DNA to introduce nucleic acids into specific primary cells.

During developing these polymers, it must be considered that polymers possess biocompatibility, specificity to target tissues or cells, high efficiency of gene transfection, low immune response and so on. Additionally, polymers must be biodegradable. Polyurethane known in the prior art is modified in some suitable process, such as adding wood flour, sugars, starch, to make polyurethane more biodegradable. PCT Pub. No. WO 89/05830 is disclosed matrix materials for tissue repairing based on biodegradable polyurethanes and polyester polyol prepolymers.

SUMMARY OF THE INVENTION

Briefly, the present invention involves a biodegradable cationic polymer with amino groups in the backbone and side chains. Therefore, the biodegradable cationic polymer is able to self-assemble complexes with nucleic acids, and delivers nucleic acids into a cell.

In another aspect of the present invention, there is provided a method of making a biodegradable cationic polymer, which comprises L-lysine and polyol in the structure for delivering nucleic acids into a cell. Therefore, no cytotoxic by-product may be generated during hydrolysis of the biodegradable cationic polymer.

In still another aspect of the present invention, there is provided a method of using a biodegradable cationic polymer, which forms complexes with nucleic acids, for in vitro delivering nucleic acids into a cell by endocytosis.

In accordance with the foregoing and other aspects of the present invention, there is provided a biodegradable cationic polymer, according to the formula ($V_a$):

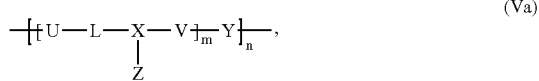

wherein

U is $(R_1-O)_d$, in which $R_1$ is a $C_2-C_{20}$ alkylene or substituted alkylene radical, d is an integer of 4 to 200,

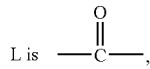

X is an amino acid group containing additional amino or amide group of the formula ($II_a$):

in which $R_8$ includes but is not limited $-CH_2CONH_2-$, $-CH_2CH_2CONH_2-$, or $-CH_2CH_2CH_2NH_2-$,
V is $-COO-$,
Y is an amino group of the formula ($VI_a$):

in which $R_2$ is hydrogen or $C_1-C_{20}$ alkyl radical, $R_3$ and $R_4$ is the same $C_1-C_{20}$ alkylene radical,
Z is an another amino group of the formula ($VII_a$):

in which $R_5$ is $C_2-C_{20}$ alkylene radical, $R_6$ and $R_7$ are the same or different $C_1-C_5$ alkyl radicals,
m is an integer of 1 to 10, and
n is an integer of 1 to 20.

In a preferred embodiment of the present invention, the molecular weight (MW) of the biodegradable cationic polymer is 6000 to 62000. In another aspect of the present invention, there is provided a method of making a biodegradable cationic polymer for delivering nucleic acids into a cell, which comprises: at first, performing a polymerization, which reacts LDI with a polyol until the first NCO/OH molar ratio in anhydrous dimethyl formamide (DMF) at 75 to 85° C., to obtain an isocyanate-terminated prepolymer; next, performing a chain extension reaction, which has decrease of 0 to 10° C., then adds the chain extender slowly to the prepolymer until the second NCO/OH molar ratio, and an organotin compound is used as a catalyst at 75 to 85° C. for approximately 120 min, to obtain a polyurethane having an alkoxide group provided by LDI; and performing an aminolysis reaction, which replaces the alkoxide group of the polyurethane with another amine, to obtain the biodegradable cationic polymer.

In a preferred embodiment of the present invention, the polyol includes but is not limited polyethylene glycol (PEG), polypropylene glycol (PPG), polytetramethylene glycol (PTMG) and polytetramethylene ester glycol (PTMEG). In still another preferred embodiment of the present invention, the first NCO/OH molar ratio is approximately 2/1.

In another preferred embodiment of the present invention, the chain extender is an amine of the formula (VI):

wherein $R_2$ is hydrogen or $C_1-C_{20}$ alkyl radical, and $R_3$ and $R_4$ are the same $C_1-C_{20}$ alkylene radical.

In still another preferred embodiment of the present invention, the organotin compound is added in 0.1 to 1 weight percent (wt %).

In another preferred embodiment of the present invention, another amine presents a formula (VII):

in which $R_5$ is $C_2-C_{20}$ alkylene radical, $R_6$ and $R_7$ are the same or different $C_1-C_5$ alkyl radicals.

In still another aspect of the present invention, there is provided a method of using a biodegradable cationic polymer, which comprises: at first, forming complexes with the nucleic acids and the biodegradable cationic polymer; and applying the complexes to the cell by endocytosis for delivering the nucleic acids into the cell; wherein the biodegradable cationic polymer has a formula ($V_a$) as above in which U, L, X, V, Y, Z, m, and n are defined as above.

In a preferred embodiment, a mass ratio of the biodegradable cationic polymer to the nucleic acids is 1/1 to 50/1.

In another preferred embodiment, the nucleic acids are encoded a gene, and the nucleic acids are DNA or RNA.

In still another preferred embodiment, the cell is a primary cell or a tumor cell.

It is to be understood that both the foregoing general description and the following detailed description are by examples, and are intended to provide further explanation of the invention as claimed.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE PREFERRED EMBODIMENT

Figure 1:
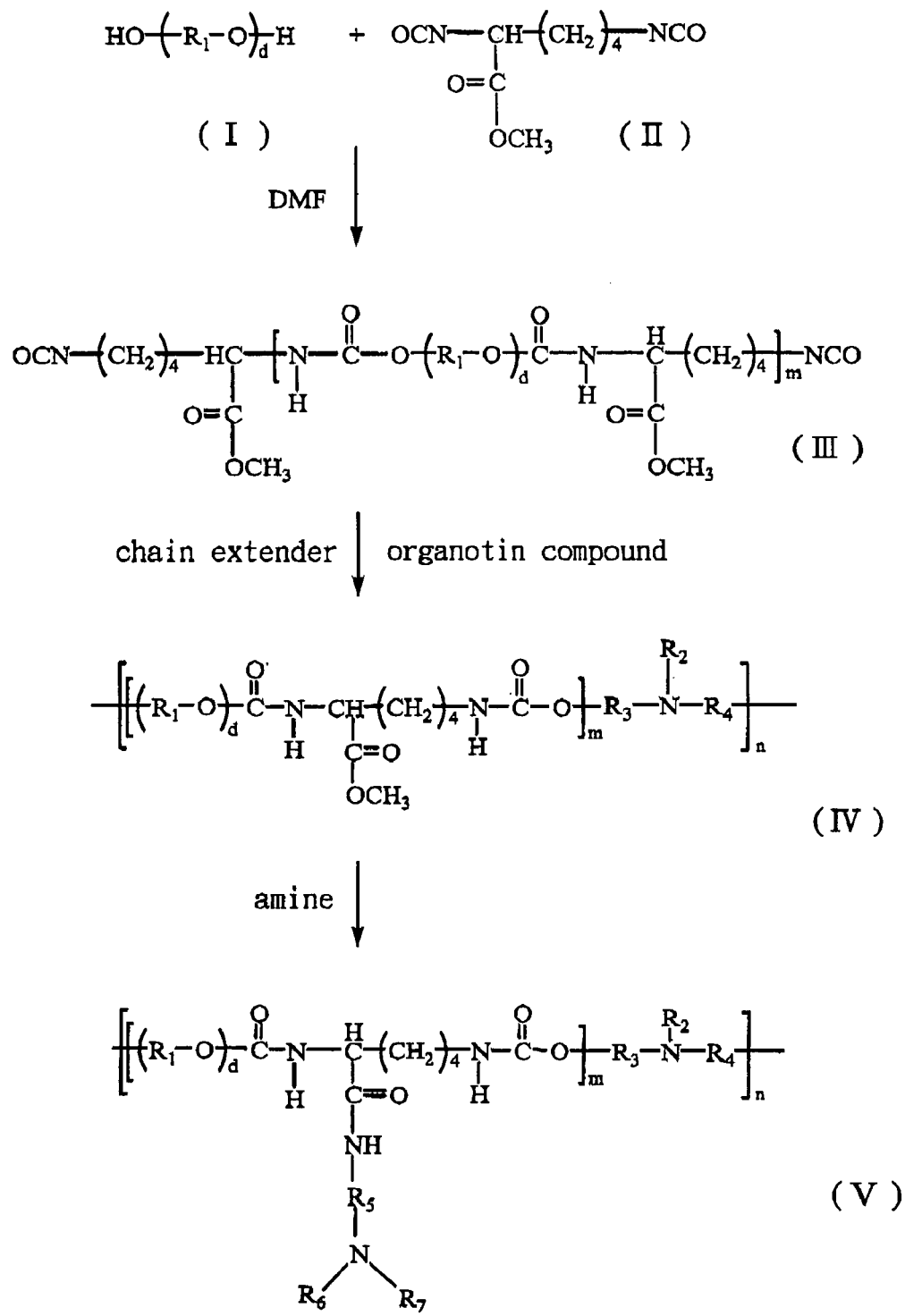
FIG. 1 is a synthetic scheme for a biodegradable cationic polymer according to one preferred embodiment of the present invention.

Reference will now be made in detail to the present preferred embodiments of the invention, and examples of the present invention are illustrated in the accompanying drawings. Wherever possible, the same reference numbers are used in the drawings and the description to refer to the same or like parts.

Herein there is provided a biodegradable cationic polymer and a method of making thereof. The biodegradable cationic polymer with amino groups in the backbone and side chains, is able to self-assemble complexes with nucleic acids, and delivers nucleic acids into a cell.

According to one preferred embodiment of the present invention, there is provided a biodegradable cationic polymer, according to the formula (V$_a$):

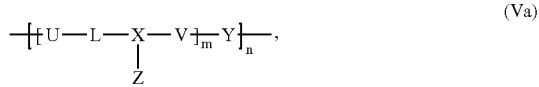

wherein

U is (R$_1$—O)$_d$, in which R$_1$ is a C$_2$–C$_{20}$ alkylene or substituted alkylene radical, d is an integer of 4 to 200, L is

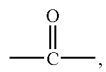

X is an amino acid group containing additional amino or amide group of the formula (II$_a$):

in which R$_8$ includes but is not limited —CH$_2$CONH$_2$—, —CH$_2$CH$_2$CONH$_2$—, or —CH$_2$CH$_2$CH$_2$NH$_2$—, V is —COO—, Y is an amino group of the formula (VI$_a$):

in which R$_2$ is hydrogen or C$_1$–C$_{20}$ alkyl radical, R$_3$ and R$_4$ is the same C$_1$–C$_{20}$ alkylene radical, Z is an another amino group of the formula (VII$_a$):

in which R$_5$ is C$_2$–C$_{20}$ alkylene radical, R$_6$ and R$_7$ are the same or different C$_1$–C$_5$ alkyl radicals, m is an integer of 1 to 10, and n is an integer of 1 to 20.

According to one preferred embodiment of the present invention, R$_1$ is preferable C$_2$–C$_5$ alkylene radicals. For instance, R$_1$ is ethylene radical, d is an integer of 4 to 200. In another case, R$_1$ is propylene radical, d is an integer of 9 to 34.

According to one preferred embodiment of the present invention, the molecular weight (MW) of the biodegradable cationic polymer is 6000 to 62000.

In addition, reference is made to FIG. 1, which is a synthetic scheme for a biodegradable cationic polymer according to one preferred embodiment of the present invention. First, polyol shown in the formula (I), and LDI shown in the formula (II) are provided, which polyol (I) has R$_1$ group that is an C$_2$–C$_{20}$ alkylene radical, preferably an C$_2$–C$_5$ alkylene radical, in which d is 4 to 200. Polyol (I) and LDI (II) are dried in the vacuum oven.

According to one preferred embodiment of the present invention, polyol (I) includes but is not limited PEG, PPG, PTMG and PTMEG. The value of d is a degree of polymerization. For instance, if polyol (I) is PEG, d is 4 to 200. In another case of the present invention, if polyol (I) is PPG, d is 9 to 34.

A polymerization reaction is subsequently performed, which reacts LDI with a polyol in anhydrous DMF at 75 to 85° C. until the first NCO/OH molar ratio, to obtain an isocyanate-terminated prepolymer of the formula (III) in FIG. 1.

According to another preferred embodiment of the present invention, the formula of the prepolymer (III) represents as below:

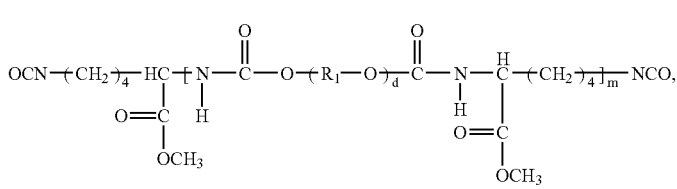

wherein m is an integer of 1 to 10.

According to one preferred embodiment of the present invention, the first NCO/OH molar ratio is such as approximately 2/1.

According to one preferred embodiment of the present invention, the polymerization reacts at approximately 80° C.

Then, a chain extension reaction is performed, which has decrease of 0 to 10° C., then adds the chain extender slowly to the prepolymer until the second NCO/OH molar ratio, and an organotin compound is used as catalyst at 75 to 85° C. for approximately 120 min, to obtain a polyurethane of the formula (IV):

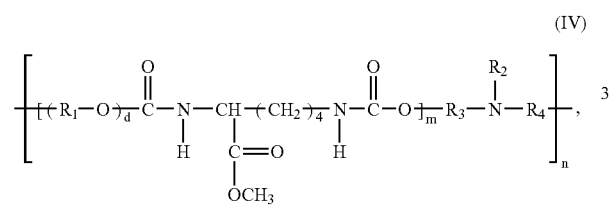

wherein the polyurethane (IV) has an alkoxide group provided by LDI (II), and n is an integer of 1 to 20.

According to one preferred embodiment of the present invention, the alkoxide group is methyloxide group.

According to another preferred embodiment of the present invention, the second NCO/OH molar ratio is such as approximately 1/1.

According to one preferred embodiment of the present invention, the chain extension reacts preferably at approximately 80° C.

According to another preferred embodiment of the present invention, the chain extender is an amine represented by the formula (VI) as below:

wherein $R_2$ is hydrogen or $C_1$–$C_{20}$ alkyl radical, $R_3$ and $R_4$ is the same $C_1$–$C_{20}$ alkylene radical.

According to another preferred embodiment of the present invention, the chain extender is preferable N-methyldiethanolamine (MDEA).

According to one preferred embodiment of the present invention, the organotin compound is preferable dibutyltin dilaurate.

According to another preferred embodiment of the present invention, the organotin compound is preferably added in 0.1 to 1 wt %, especially in 0.5 wt %.

Later, an aminolysis reaction is performed, which the alkoxide group of the polyurethane (IV) is replaced by an amino group with another amine, to obtain the biodegradable cationic polymer, which has a formula (V):

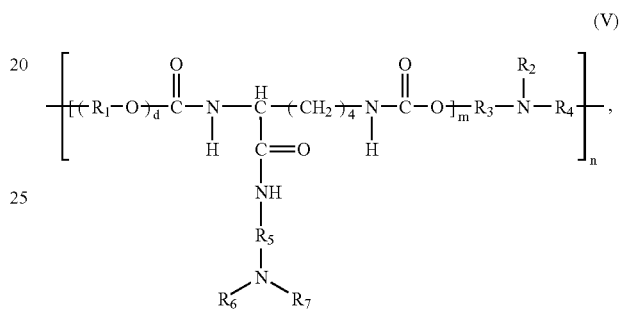

wherein n is an integer of 1 to 20, and the amino group is bound to nucleic acids for delivering nucleic acids into a cell.

In a preferred embodiment of the present invention, the molecular weight (MW) of the biodegradable cationic polymer (V) is 6000 to 62000.

According to one preferred embodiment of the present invention, the another amine represents a formula (VII) as below:

wherein $R_5$ is $C_2$–$C_{20}$ alkylene radical, $R_6$ and $R_7$ is the same or different $C_1$–$C_5$ alkyl radical.

According to one preferred embodiment of the present invention, the another amine is preferable N,N-diethylethylenediamine (DEDA).

As mentioned above, the present invention further provides a method of using a biodegradable cationic polymer for in vitro delivering nucleic acids into a cell, which forms complexes with the nucleic acids for delivering the nucleic acids into the cell by endocytosis.

According to one preferred embodiment of the method of using a biodegradable cationic polymer for in vitro delivering nucleic acids into a cell of the present invention, at first, nucleic acids and the biodegradable cationic polymer are formed to the complexes. The biodegradable cationic polymer is dissolved in 20 mM N-2-hydroxyethyl-piperazine-N'-2-ethane sulfonic acid (Hepes) buffer (pH 7.4), then add the biodegradable cationic polymer solution rapidly into the nucleic acids-containing solution, for reacting nucleic acids and the biodegradable cationic polymer in Hepes buffer at room temperature for 30 minutes.

Next, apply the complexes to a cell, which uses the complexes to deliver nucleic acids into the cell by endocytosis; and in which the biodegradable cationic polymer represents the formula ($V_a$) as below:

$$\{\{U-L-X-V\}_m-Y\}_n,\quad (Va)$$
$$\qquad\ \ \ |$$
$$\qquad\ \ \ Z$$

wherein

U is $(R_1-O)_d$, in which $R_1$ is a $C_2-C_{20}$ alkylene or substituted alkylene radical, d is an integer of 4 to 200, L is $$-\overset{O}{\underset{\|}{C}}-,$$

X is an amino acid group containing additional amino or amide group of the formula ($II_a$), $$-HN-\underset{\underset{C=\!\!=\!O}{|}}{CH}-R_8-\qquad (IIa)$$

in which $R_8$ includes but is not limited —$CH_2CONH_2$—, —$CH_2CH_2CONH_2$—, or —$CH_2CH_2CH_2NH_2$—, V is —COO—, Y is an amino group of the formula ($VI_a$)

$$-R_3-\underset{\underset{R_4}{|}}{\overset{\overset{R_2}{|}}{N}}-,\qquad (VIa)$$

in which $R_2$ is hydrogen or $C_1-C_{20}$ alkyl radical, $R_3$ and $R_4$ is the same $C_1-C_{20}$ alkylene radical, Z is an another amino group of the formula ($VII_a$), $$\begin{array}{c}|\\NH\\|\\R_5\\|\\R_6-N-R_7\end{array}\qquad (VIIa)$$

in which $R_5$ is $C_2-C_{20}$ alkylene radical, $R_6$ and $R_7$ are the same or different $C_1-C_5$ alkyl radicals, m is an integer of 1 to 10, and n is an integer of 1 to 20.

Preferable example of the biodegradable cationic polymer of the formula (V) the present invention comprises:

$$\left[\{(R_1-O)_d-\overset{O}{\underset{\|}{C}}-N-\underset{\underset{\underset{\underset{R_6\ \ R_7}{\diagdown N\diagup}}{|}}{\underset{R_5}{|}}}{\underset{C=O}{\underset{|}{CH}}}-(CH_2)_4-N-\overset{O}{\underset{\|}{C}}-O\}_m-R_3-\underset{\underset{R_4}{|}}{N}-\right],\qquad (V)$$

wherein $R_1$, $R_2$, $R_3$, $R_4$, $R_5$, $R_6$, $R_7$, d, m, and n are defined as above.

According to one preferred embodiment of the present invention, $R_1$ is preferable $C_2-C_5$ alkylene radical. For instance, $R_1$ is ethylene radical, d is an integer of 4 to 200. In another case, $R_1$ is propylene radical, d is an integer of 9 to 34.

According to one preferred embodiment of the present invention, a mass ratio of the biodegradable cationic polymer to the nucleic acids is preferably 1/1 to 50/1, more preferably 5/1 to 30/1, especially preferably 20/1.

According to one preferred embodiment of the present invention, the nucleic acids are encoded a gene, and the nucleic acids are DNA or RNA. According to another preferred embodiment of the present invention, the DNA is such as double-stranded DNA, single-stranded DNA or synthetic oligonucleotides, and the RNA is such as sense RNA, anti-sense RNA or ribozyme RNA.

According to one preferred embodiment of the present invention, the cell is a tumor cell or a primary cell.

The following examples illustrate various embodiments of the invention, and are not to be interpreted as limiting the scope of the appended claims. In the examples all parts are by weight unless otherwise specified.

EXAMPLE 1

Synthesis of Prepolymer

Polymerizations are conducted in a three-necked reaction flask under dry nitrogen purge according to a standard two-step process well known in the art. LDI (II) (from Kyowa Hakko Kogyo Co., Ltd) and PEG 200 (I) (MW=200 g/mol, from Showa Co., Ltd) as shown in FIG. 1 are dried in a vacuum oven, then prepolymerized in anhydrous DMF at approximately 80° C. until 2/1 of NCO/OH molar ratio, to obtain an isocyanate-terminated prepolymer of the formula (III) in the FIG. 1. The NCO content is determined by di-n-butylamine titration during prepolymerization.

EXAMPLE 2

Synthesis of Polyurethane

The resulting prepolymer has decrease of 0 to 10° C., then a chain extension is carried out by adding MDEA slowly to the prepolymer until 1/1 of NCO/OH molar ratio, and using 0.5 wt % dibutyltin dilaurate as a catalyst at approximately 80° C. for approximately 120 min until the unreacted isocynate group is not observed, to obtain a polyurethane.

EXAMPLE 3

Synthesis of DEDA-PU

An aminolysis reaction is performed, which replaces the methyloxide group of the resulting polyurethane with DEDA. 100 g of the resulting polyurethane is dissolved in 1 liter of anhydrous DMF, then excess DEDA is slowly added into the DMF solution of polyurethane stirring at least for 48 hours. Under reduced pressure, the methyloxide group provided by LDI of the resulting polyurethane is replaced by DEDA to form DEDA-PU. The resulting DEDA-PU is precipitated in cold ethyl ether and then dried at 50° C. under vacuum.

Figure 2:
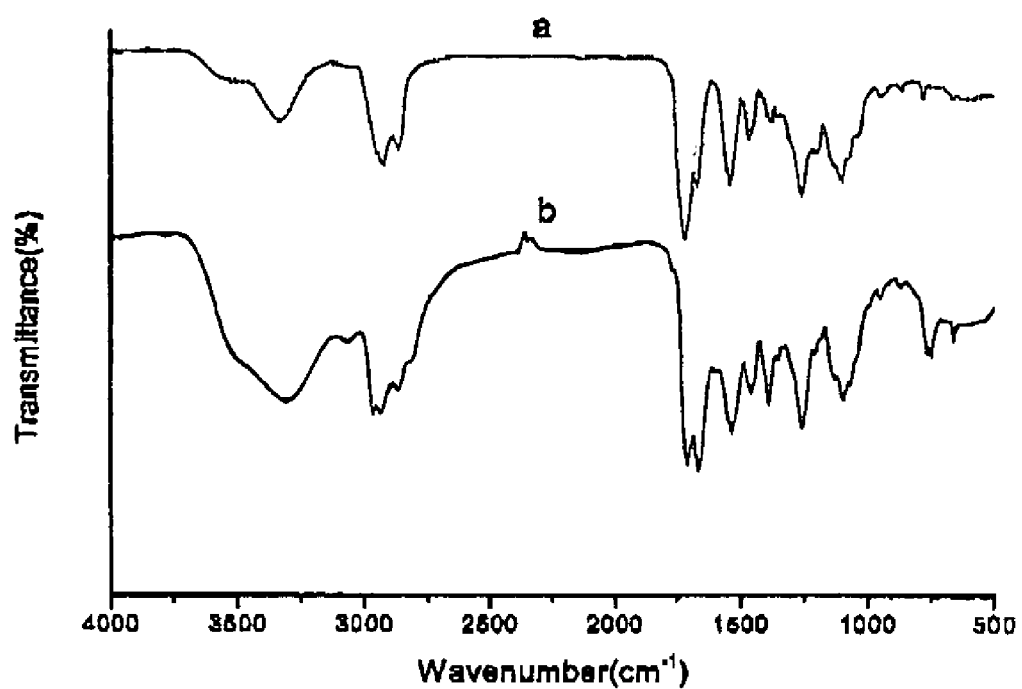
FIG. 2 is a FT-IR spectrum of DEDA-PU according to one preferred embodiment of this invention.

The resulting DEDA-PU is characterized and analyzed with Fourier transform infrared (FT-IR) spectrometer (Perkin-Elmer 824) and nuclear magnetic resonance (NMR) spectrometer (Varian UnityInova 500-Hz). Reference is made in FIG. 2, which is an FT-IR spectrum of DEDA-PU according to one preferred embodiment of this invention. A strong absorption peak of the curve (a) of the polyurethane at 2250 $cm^{-1}$, before polymerization, corresponding to the —NCO group of the LDI monomer, was absent after the chain extension shown as the curve (b), indicating the polymerization is successful. In addition, the urethane peaks of polyurethane appeared at 1720 $cm^{-1}$ (—C═O stretching, urethane), 1662 $cm^{-1}$ (—C═O stretching, amide I), 1535 $cm^{-1}$ (—N—H bending, amide II), and 3340 $cm^{-1}$ (—N—H stretching, urethane).

Figure 3A:
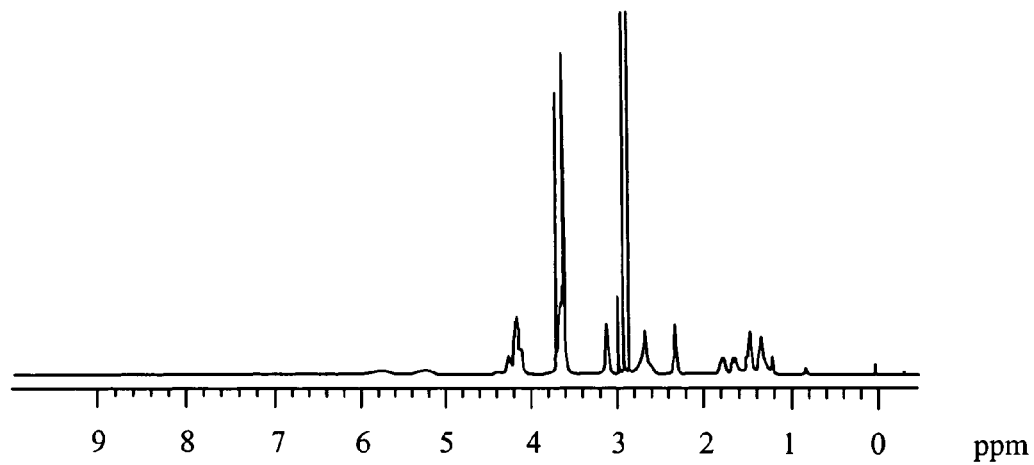
FIGS. 3(a) and 3(b) are $^1$H-NMR spectra of DEDA-PU according to one preferred embodiment of this invention.
Figure 3B:
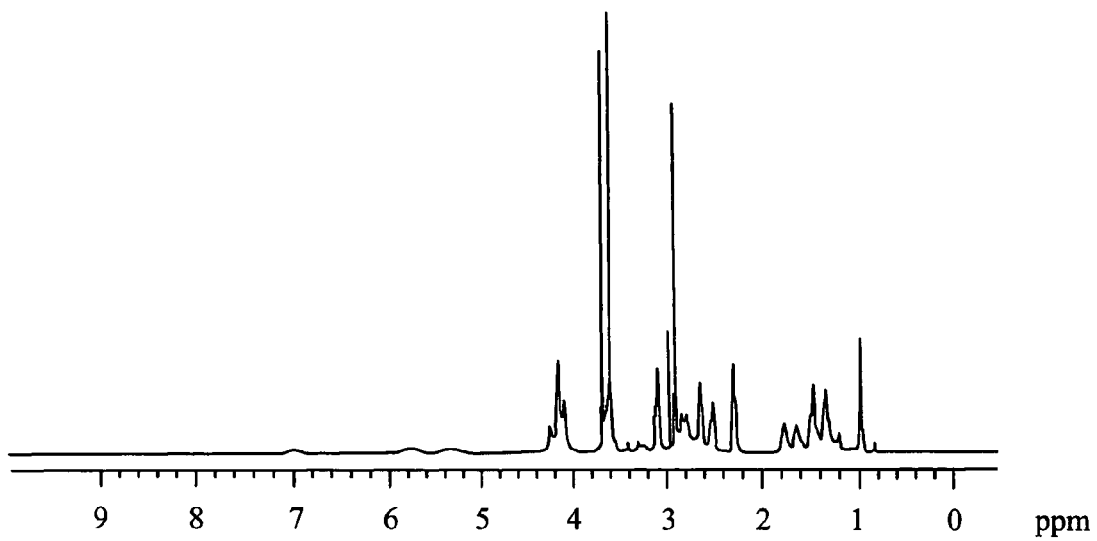

Reference is made in FIGS. 3(a) and 3(b), which are $^1$H-NMR spectra of DEDA-PU according to one preferred embodiment of this invention. In FIG. 3(a), two distinct peaks at 5.7 and 5.3 ppm are assigned to the urethane NH protons derived from the α- and ε-amino groups of L-lysine, respectively. In FIG. 3(b), the peaks at 3.6 and 2.8 ppm are assigned to the methylene protons in the main backbone chain of PEG and the chain extender MDEA, respectively.

Reference is made in FIG. 2 again, which is an FT-IR spectrum of DEDA-PU according to one preferred embodiment of this invention. In the FT-IR spectrum, the intensity of C═O stretching band increased relative to the amide I peak of polyurethane at 1662 $cm^{-1}$, when the amide linkage of pendent group is included. In FIG. 3(b), the peaks at 0.9 and 7.0 ppm are assigned to the methyl and amide protons derived from the pendant group of DEDA-PU, respectively. An identical observation is made in the $^{13}$C-NMR spectrum shown that the peaks at 10.8 and 162.8 ppm (data not shown). And disappearance of the peak at 172.2 ppm in the ester group of polyurethane is clear indication of the successful aminolysis reaction of the pendant group of polyurethane.

Figure 4:
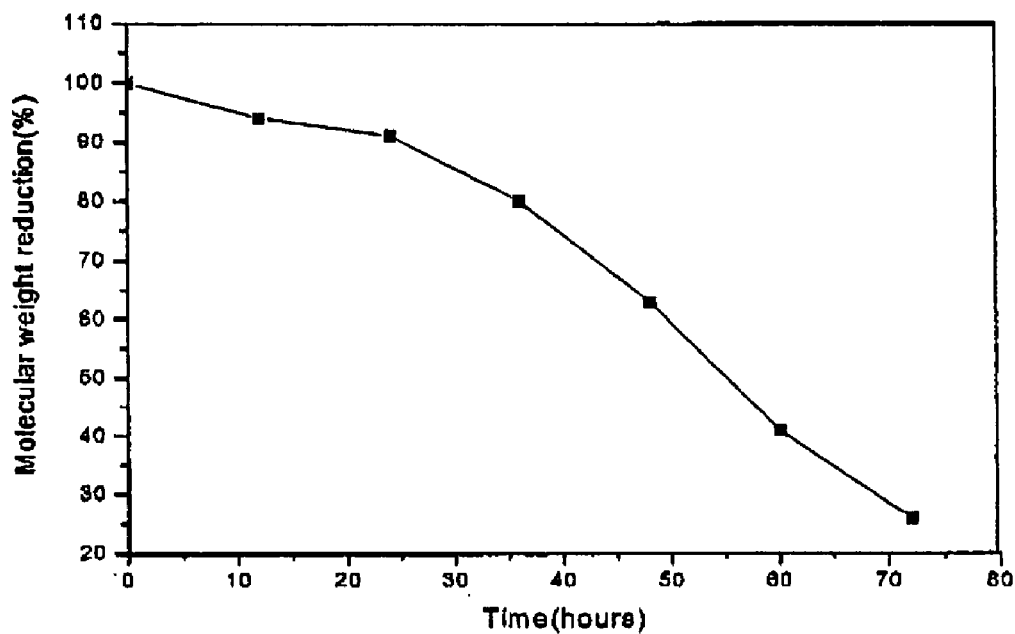
FIG. 4 is a plot showing molecular weight changes with degrading time of DEDA-PU during hydrolytic degradation of DEDA-PU in various durations according to one preferred embodiment of this invention.

The hydrolytic degradation of the resulting DEDA-PU is further analyzed. 20 mg/ml of DEDA-PU is dissolved in the 20 mM Hepes buffer (pH 7.4) and incubated in the water bath at 37° C. After hydrolysis for various time and then vacuum dried for several hours, the molecular weight is determined by high performance liquid chromatography/gel permeation chromatography (HPLC/GPC). The weight-average molecular weight ($\overline{Mw}$) of un-degraded DEDA-PU is 12,600, the number-average molecular weight ($\overline{Mn}$) is 8,100, and the polydispersity index is 1.56. According to one preferred embodiment of the present invention. DEDA-PU is degraded during various time, the relationship of the degradation time and the molecular weight is shown in the FIG. 4. After degradation of DEDA-PU, the change in molecular weight is caused by hydrolytic degradation in liable urethane part of the polymer, and the diisocyanate in the polymer is converted into non-toxic lysine. It is shown the rate of degradation at the first 24 hours is comparatively slower than subsequent 48 hours. Since the degraded polymer has shorter chain and more hydroxyl and amine end groups, they could accelerate degradation rates via nucleophilic attack on urethanes. Moreover, an introduction of PEG segments increased the hydrophilicity and flexibility of the polymer, which promoted the susceptibility to hydrolysis. Therefore, a shorter DEDA-PU resulting PEG segments easily exposed to water milieu speeds the degradation rate of the polymer.

EXAMPLE 4

Purification of Plasmid DNA

The term "plasmid DNA" used in the present invention is such as pCMV-Luc which uses a Cytomegalovirus (CMV) promoter to drive the firefly luciferase (Luc) gene expression, or pCMV-LacZ which uses a CMV promoter to drive the β-galactosidase (LacZ) gene expression. These two circular plasmid DNAs also encode an ampicillin resistant gene. The plasmid DNA is amplified in *Escherichia coli* (DH5α strain) and purified by column chromatography (from Qiagen® Plasmid Mega kit, Germany). The purified plasmid DNA is dissolved in the tris(hydroxymethyl)methylamine-ethylenediaminetetraacetic acid (Tris-EDTA) buffer (pH 8.0) and determined by the ratio of ultraviolet (UV) absorbance at 260 nm/280 nm. The ratio of absorbance at 260 and 280 nm for plasmid DNA is between 1.8 and 2.0. The concentrations of the plasmid DNA is determined by using the equation as below:

1.0 unit of the optical density (OD) detected from the DNA solution at the wavelength 260 nm
(1.0 $OD_{260}$)=50 µg/ml of the plasmid DNA.

pCMV-Luc and pCMV-LacZ are well known in the prior art, and pCMV-Luc and pCMV-LacZ are provided for exemplary illustrations, but not limited to the description of the preferred embodiments container herein. For instance, linear dsDNA, ssDNA, synthetic oligonucleotides, sense RNA, anti-sense RNA, ribozyme RNA or the like, can form complexes with the biodegradable cationic polymer of the present invention within the scope of the spirit and scope of the appended claims.

EXAMPLE 5

Cell Cuture

Human embryonic kidney 293 cells (HEK 293) are obtained from Americam Type Culture Collection (ATCC). The HEK 293 cells are cultured in the Dulbecco's modified Eagle's medium (DMEM, from GibcoBRL Co., Ltd.) supplemented with 10% heated-inactivated horse serum, streptomycin at 100 µg/ml, penicillin at 100 U/ml, 1.5 g/L sodium hydrogen carbonate, 1 mM sodium pyruvate, and 2 mM L-glutamine, and maintained at 37° C. in a humidified 5% $CO_2$-containing atmosphere.

EXAMPLE 6

Preparation of DEDA-PU/DNA Complexes 5.0 mg/ml of DEDA-PU is prepared in the 20 mM Hepes buffer (pH 7.4) and its serial dilutions are made. Next, the DEDA-PU serial dilutions are added rapidly into the DNA solutions to obtain DEDA-PU/DNA complexes, in which the mass ratio of DEDA-PU/DNA (w/w) is 1/2 to 100/1. The above mass ratios of the DEDA-PU/DNA complexes are all in a range where visible aggregation was not observed. And then, the complexes are allowed to self-assemble in the Hepes buffer and incubated at room temperature for 30 minutes.

Figure 5:
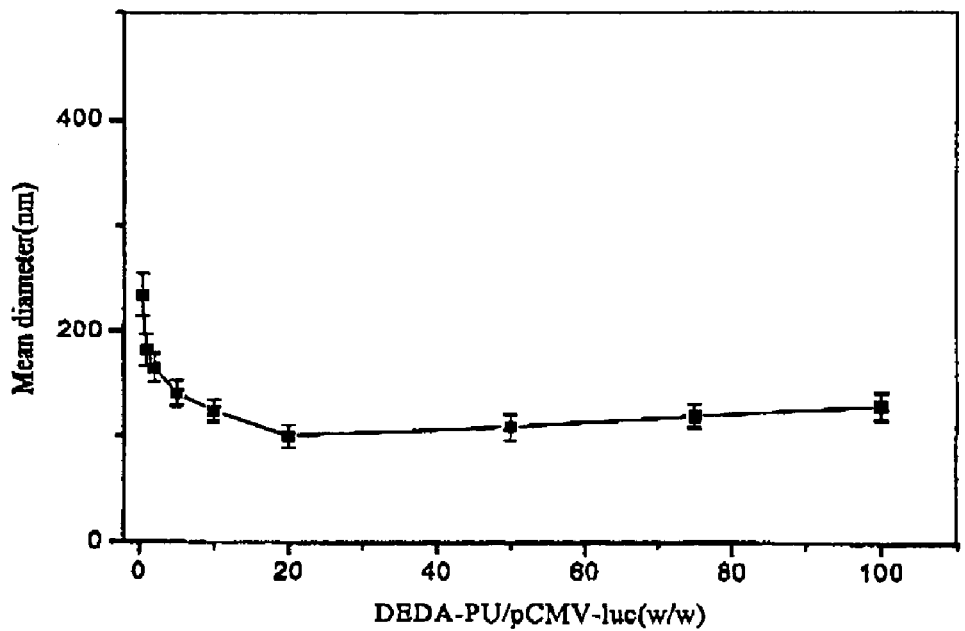
FIG. 5 is a plot showing size changes with mass ratios of DEDA-PU/DNA complexes according to one preferred embodiment of this invention.

The mean diameter and size distribution of the resulting DEDA-PU/DNA complexes are determined by the dynamic light scattering (DLS) at 25° C. DEDA-PU and DNA, attracting to each other due to opposite charge attraction, can form complexes. Various mass ratios of DEDA-PU/DNA complexes are measured by DLS spectrometer. The hydrodynamic size of the DEDA-PU/DNA complexes are further measured by the DLS spectrometer using a low power of 5 mW, He—Ne laser ($\lambda$=633 nm) as the incident beam at the scattering angle of 90°. The hydrodynamic radius, $R_H$ is calculated from the average collective diffusion coefficient, Dav, using the Einstein-Stokes equation:

$$R_H = \kappa T / 6\pi\eta Dav$$

where $\kappa$ is the Boltzmann constant, T is absolute temperature and $\eta$ (0.933 cP) is the viscosity of water at 25° C. DEDA-PU/DNA complexes are prepared using the same concentration of pCMV-Luc (10 µg/ml) with addition of DEDA-PU for varying mass ratios. FIG. 5 is a plot showing size changes with mass ratios of DEDA-PU/DNA complexes according to one preferred embodiment of this invention. The results are shown that the size of the resulting complexes is smaller, approximately 100 nm, at 20/1 of the mass ratio of DEDA-PU to DNA. A further increase in the amount of DEDA-PU does not affect the size of complexes.

The optimal mass ratio of DEDA-PU to complexate and condense DNA, is further analyzed by gel retardation assay, in which the DEDA-PU/DNA complexes are loaded into a 0.7% agarose gel containing ethidium bromide (EtBr; 0.6 µg/ml) in Tris-Acetate-EDTA (TAE) buffer and performed at 100V for 90 minutes. After electrophoresis, the band is visualized by UV-irradiation. The results are shown in lanes 1 to 5 of FIG. 6. Free DNA is shown in lane 1 as indicated by the arrow 10. The degraded DEDA-PU/DNA complexes degraded by hydrolysis are shown in lanes 2 and 3 as indicated by the arrow 11. The undegraded DEDA-PU/DNA complexes are shown in lanes 4 and 5 as indicated by the arrow 12. DNA is partially retained by the presence of DEDA-PU at a mass ratio of 1/1 (lane 4) and totally retained at a mass ratio of 50/1 (lane 5) as indicated by the arrow 12, and the residual released DNA in lane 4 is indicated by the arrow 10. These results reveal that amine groups of DEDA-PU carrying positive charges interacted with DNA phosphate groups with negative charges to form neutral-close self-assembly complexes.

Figure 6:
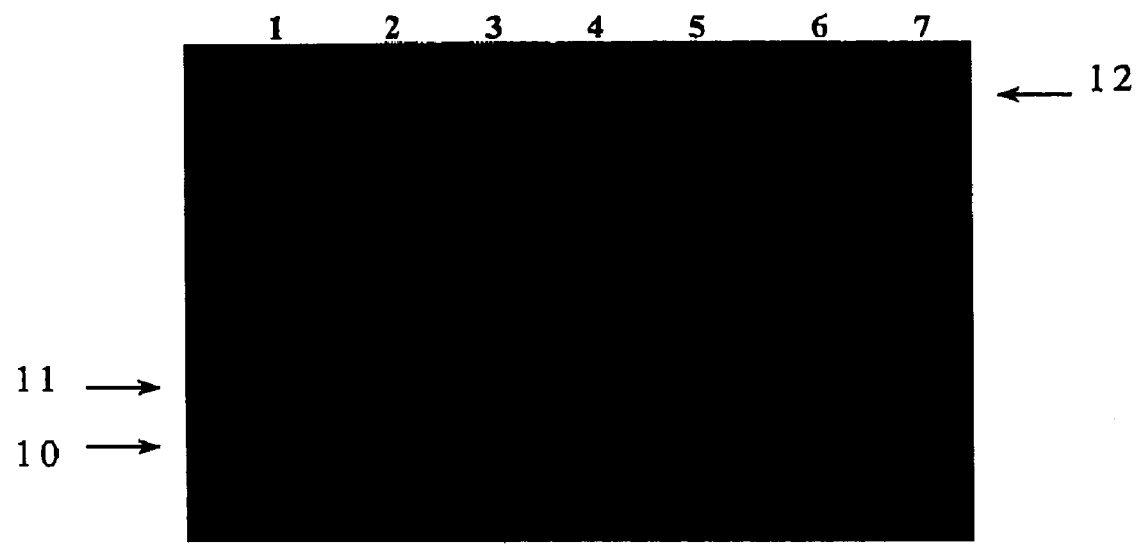
FIG. 6 is an electrophoretic assay of DEDA-PU/DNA complexes according to one preferred embodiment of this invention.

The hydrolytic ability of the resulting DEDA-PU complexes is further analyzed by restriction endonuclease protection assay. The DEDA-PU complexes are incubated with Hind III or Kpn I at a concentration of 10 U/µl at 37° C. for 90 minutes in their provided reaction buffer. After the certain restriction endonuclease digesting, the products analyzed by agarose gel electrophoresis in the same manner as described above are shown in lanes 6 and 7 of FIG. 6. The restriction endonucleases Hind III and Kpn I, which cleaved the plasmid DNA in the CMV-promoter region and the ampicillin resistance region, respectively. The treatments generate the linear-forms of the plasmid DNA in lanes 2 and 3 as shown in FIG. 6, respectively. However, it is observed that the plasmid DNA is completely protected against Hind III and Kpn I when the presence of DEDA-PU in complexes is at a mass ratio of 50/1, as indicated by the arrow 12 in lanes 6 and 7 of FIG. 6. Reference is made to FIG. 5, the DEDA-PU/DNA complexes at a mass ratio of 50/1 are shown relatively small particle size and condense DNA.

Figure 7:
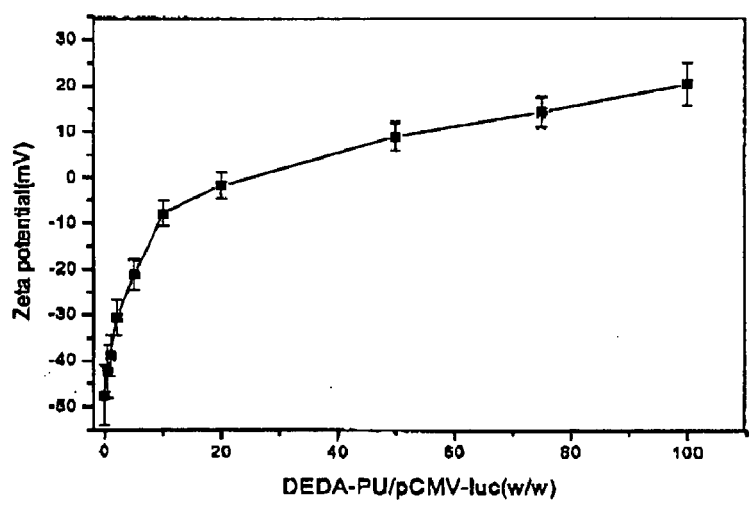
FIG. 7 is a plot showing zeta potential changes with mass ratios of DEDA-PU/DNA complexes according to one preferred embodiment of this invention.

On the other hand, the surface charges of the DEDA-PU/DNA complexes are conducted by determining the electrophoretic mobility at a temperature of 25° C. with Zeta potential system (Nicomp Instrument, U.S.A.). Refractive index and viscosity used in determination are assumed to be the same as for water. FIG. 7 is a plot showing zeta potential changes with mass ratios of DEDA-PU/DNA complexes according to one preferred embodiment of this invention. The Zeta potential of the resulting complexes changes from negative charge to a positive charge when the amount of DEDA-PU is increased. At a mass ratio of 50/1 of DEDA-PU/DNA complexes, particles of less positive potential are obtained. The result is in agreement with those obtained in DNA gel retardation assay where the DEDA-PU/DNA complexes are completely retained in gel at the same ratio. These complexes carry extra positive charges on their surfaces, which in turn allow better interaction with target cell membrane and therefore an enhanced uptake.

EXAMPLE 7

Cytotoxicity of DEDA-PU/DNA Complexes on Cells

The cytotoxicity of DEDA-PU, degraded DEDA-PU and DEDA-PU/DNA complexes on 293 cells is assessed with XTT assay. Metabolization of XTT (sodium(2,3-bis(2-methoxy-4-nitro-5-sulphophenyl)-2H-tetrazolium-5-carboxanilide) to an orange water-soluble formazan dye is formed by mitochondrial dehydrogenease activity of living cells, for evaluating cytotoxicity of DEDA-PU, degraded DEDA-PU, and DEDA-PU/DNA complexes on cells.

The 293 cells are cultured in complete DMEM then seeded at a density of $1\times10^4$ cell/well in a 96-well plate. The cells are incubated at 37° C. and 5% $CO_2$ in humidified atmosphere for 24 hours. Subsequently, the cells are incubated for one hour in 200 µl DMEM containing sterile DEDA-PU, degraded DEDA-PU and DEDA-PU/pCMV-Luc with various concentrations, respectively. The cells are incubated in DMEM only for a negative control. After one hour, the cells are replaced by complete DMEM for further 48 hour incubation. Then, 50 µl XTT labeling mixture [containing 5 ml of 5 mg/ml XTT stock solution and 0.1 ml electro-coupling reagent (PMS)] is added to each well and incubated at 37° C. for one hour. Cell Viability is calculated from measured cell numbers by establishing the calibration curve of plating known numbers of cells (0 to $1\times10^5$ cells/well) two hours prior to adding XTT reagent into wells. Absorbance of the supernatant at 490 nm (690 nm as a reference wavelength) is then measured using an enzyme-linked immunosorbent assay (ELISA) reader. Results are shown in FIG. 8, which is the relatively cell viability (%) with respect to control wells containing DMEM without DEDA-PU nor DEDA-PU/DNA complexes.

Figure 8A:
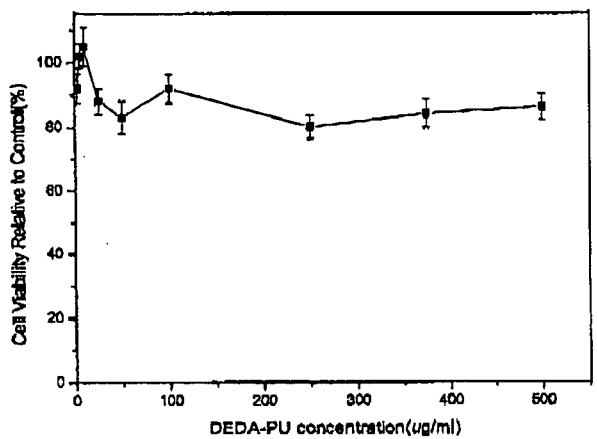
FIG. 8(a) to 8(c) are cytotoxic assays of DEDA-PU/DNA complexes according to one preferred embodiment of this invention.
Figure 8B:
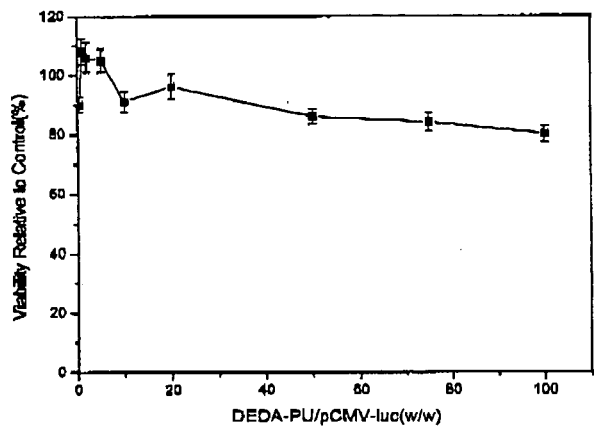
Figure 8C:
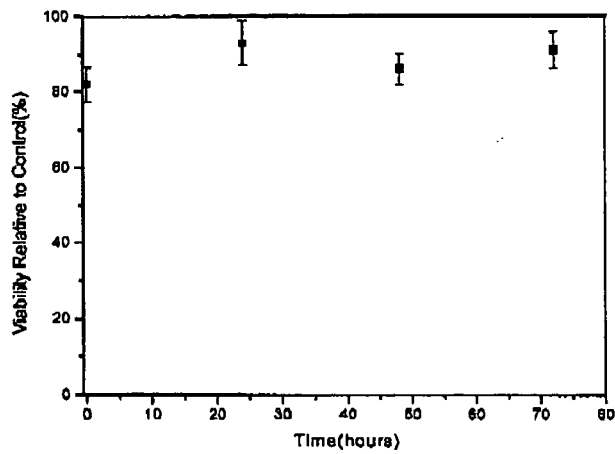

Cumulative cellular exposure time plays a primary role in the cytotoxicity of non-degradable or slowly degradable polycations. The cytotoxicity of the polycations may also influence the gene expression in interfering with transcription and translation process in the cells. The effects of DEDA-PU, degraded DEDA-PU and DEDA-PU/DNA complexes on cell viability are monitored by using XTT assay. After testing the polycation concentration, DEDA-PU and DEDA-PU/DNA complexes are no significant cytotoxicity on 293 cells. As shown in FIGS. 8(a) and 8(b), respectively, the range of the relative cell viability in the presence of DEDA-PU and DEDA-PU/DNA complexes is 0.8 to 1.1-fold of untreated control cells in all experiments. Moreover, cytotoxicity of the oligomeric products of DEDA-PU degradation is also examined. After predetermined degradation time intervals, 250 μg/ml the oligomeric products of DEDA-PU/DNA degradation revealed no cytotoxic effect on 293 cells, as shown in FIG. 8(c).

It is noticed that the cell viability is still high when the concentration of the oligomeric products of DEDA-PU is until 500 μg/ml, hence DEDA-PU can be regarded as a promising biomaterial for its biocompatibility.

EXAMPLE 8

Transfection Efficiency of DEDA-PU/DNA Complexes

Figure 9:
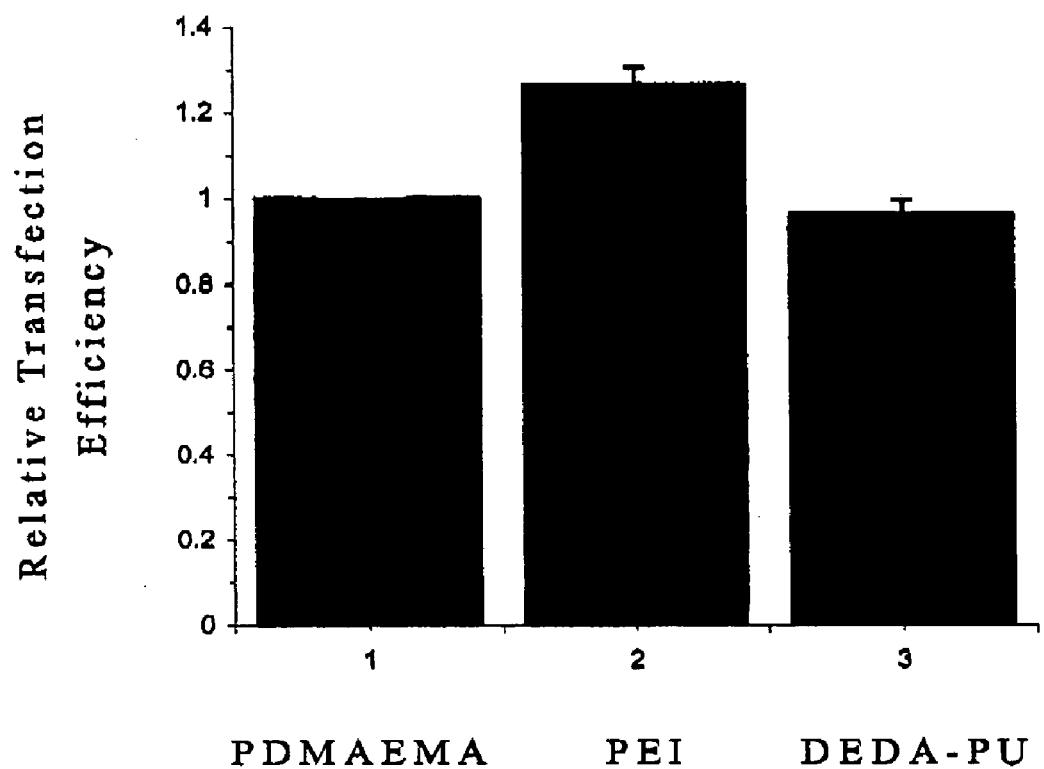
FIG. 9 is a plot of relative transfection efficiency of tumor cells with DEDA-PU/DNA complexes according to one preferred embodiment of this invention, which compares with commercial PEI and PDMAEMA.

The 293 cells are incubated in a serum-free medium containing DEDA-PU/DNA complexes for a period of time. After changing to a fresh and complete medium, the cells are continuing to be incubated. On various intervals after transfection, the cells are harvested for carrying out various observations, and the resulting data are compared with commercialized reagents, such as polyethylenimine (PEI) and poly(2-dimethylamino)ethyl methylacrylate (PDMAEMA), and shown in FIG. 9.

The results are shown that the transfection efficiency of DEDA-PU complexes of the present invention is approximately as similar as PEI and PDMAEMA.

According to the forgoing preferred embodiments, the method of making the biodegradable cationic polymer is applied to make the biodegradable cationic polymer with amino groups in the backbone and side chains. Therefore, the biodegradable cationic polymer is able to self-assemble complexes with nucleic acids, and delivers nucleic acids into a cell by endocytosis.

According to the forgoing preferred embodiments, the biodegradable cationic polymer of the present invention, which comprises LDI and polyol in the structure for delivering nucleic acids into a cell. During hydrolytic degradation of the biodegradable cationic polymer, no cytotoxic by-product may be generated. Therefore, the biodegradable cationic polymer has very low cytotoxicity.

Although the present invention has been described in considerable detail with reference certain preferred embodiments thereof other embodiments are possible. Therefore, their spirit and scope of the appended claims should no be limited to the description of the preferred embodiments container herein. In view of the foregoing, it is intended to cover modifications and variations included within the spirit and scope of the appended claims, the scope of which should be accorded the broadest interpretation so as to encompass all such modifications and similar structures.

What is claimed is:

1. A biodegradable cationic polymer, which has amino groups in a backbone and side chains for delivering nucleic acids into a cell, and a formula ($V_a$) of the biodegradable cationic polymer shown as below:

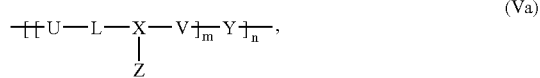

(Va)

wherein

U is $(R_1-O)_d$, in which $R_1$ is a $C_2-C_{20}$ alkylene or substituted alkylene radical, d is an integer of 4 to 200, L is

X is an amino acid group containing additional amino or amide group of the formula ($II_a$):

(IIa)

in which $R_8$ is selected from the group consisting of $-CH_2\ CONH_2-$, $-CH_2CH_2CONH_2-$, and $-CH_2CH_2CH_2NH_2-$, V is $-COO-$, Y is an amino group of the formula ($VI_a$):

(VIa)

in which $R_2$ is hydrogen or $C_1-C_{20}$ alkyl radical, $R_3$ and $R_4$ is the same $C_1-C_{20}$ alkylene radical, Z is an another amino group of the formula ($VII_a$):

(VIIa)

in which $R_5$ is $C_2-C_{20}$ alkylene radical, $R_6$ and $R_7$ are the same or different $C_1-C_5$ alkyl radicals, m is an integer of 1 to 10, and n is an integer of 1 to 20.

2. The biodegradable cationic polymer of claim 1, wherein $R_1$ is selected from the group consisting of $C_2-C_5$ alkylene radicals.

3. The biodegradable cationic polymer of claim 2, wherein $R_1$ is ethylene radical, d is an integer of 4 to 200.

4. The biodegradable cationic polymer of claim 2, wherein $R_1$ is propylene radical, d is an integer of 9 to 34.

5. The biodegradable cationic polymer of claim 1, wherein x is $-CH_2CH_2CH_2NH_2-$.

6. A biodegradable cationic polymer, which has amino groups in a backbone and side chains for delivering nucleic acids into a cell, and a formula (V) of the biodegradable cationic polymer shown as below:

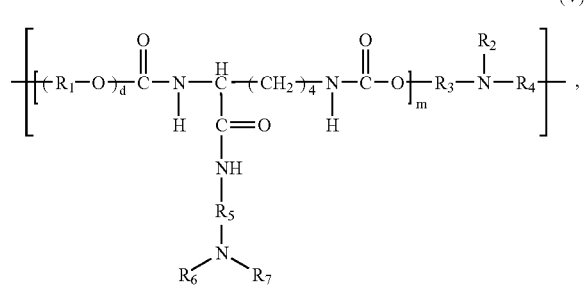

wherein

R$_1$ is a C$_2$–C$_{20}$ alkylene or substituted alkylene radical, d is an integer of 4 to 200, R$_2$ is hydrogen or C$_1$–C$_{20}$ alkyl radical, R$_3$ and R4 is the same C$_1$–C$_{20}$ alkylene radical, R$_5$ is C$_2$–C$_{20}$ alkylene radical, R$_6$ and R$_7$ is the same or different C$_1$–C$_5$ alkyl radical, m is an integer of 1 to 10, and n is an integer of 1 to 20.

7. The biodegradable cationic polymer of claim 6, wherein R$_1$ is selected from the group consisting of C$_2$–C$_5$ alkylene radicals.

8. The biodegradable cationic polymer of claim 7, wherein R$_1$ is ethylene radical, d is an integer of 4 to 200.

9. The biodegradable cationic polymer of claim 7, wherein the R$_1$ is propylene radical, d is an integer of 9 to 34.

* * * * *

UNITED STATES PATENT AND TRADEMARK OFFICE
CERTIFICATE OF CORRECTION

PATENT NO. : 7,179,874 B2 Page 1 of 1
APPLICATION NO. : 10/717713
DATED : Febraury 20, 2007
INVENTOR(S) : Min-Da Shau et al.

It is certified that error appears in the above-identified patent and that said Letters Patent is hereby corrected as shown below:

Title page, Item (73) Assignee:

Please amend the Assignee as follows from "Chia Nan University of Pharmacy and Science" to --CHIA NAN UNIVERSITY OF PHARMACY AND SCIENCY--

Signed and Sealed this

Twenty-sixth Day of June, 2007

JON W. DUDAS
*Director of the United States Patent and Trademark Office*